(12) United States Patent
Bhansali

(10) Patent No.: US 8,262,729 B2
(45) Date of Patent: Sep. 11, 2012

(54) DYNAMIC OSSICULAR PROSTHESIS

(75) Inventor: Sanjay A. Bhansali, Atlanta, GA (US)

(73) Assignee: Enteroptyx, Memphis, TN (US)

( * ) Notice: Subject to any disclaimer, the term of this patent is extended or adjusted under 35 U.S.C. 154(b) by 489 days.

(21) Appl. No.: 12/496,697

(22) Filed: Jul. 2, 2009

(65) Prior Publication Data

US 2010/0010629 A1    Jan. 14, 2010

Related U.S. Application Data

(60) Provisional application No. 61/078,929, filed on Jul. 8, 2008.

(51) Int. Cl.
*A61F 2/18* (2006.01)
(52) U.S. Cl. .......................................................... 623/10
(58) Field of Classification Search .................... 623/10; 600/25
See application file for complete search history.

(56) References Cited

U.S. PATENT DOCUMENTS

| | | |
|---|---|---|
| 1,849,604 A | 3/1932 | Weatherhead, Jr. |
| 3,710,399 A | 1/1973 | Hurst |
| 4,601,723 A | 7/1986 | McGrew |
| 4,624,672 A | 11/1986 | Lenkauskas |
| 4,641,651 A | 2/1987 | Card |
| 4,921,498 A | 5/1990 | Bays et al. |
| 5,061,280 A | 10/1991 | Prescott |
| 5,104,401 A | 4/1992 | Kurz |
| 5,350,399 A | 9/1994 | Erlebacher et al. |
| 5,458,608 A | 10/1995 | Wortich |
| 5,514,177 A | 5/1996 | Kurz et al. |
| 5,554,188 A * | 9/1996 | Prescott ........................... 623/10 |
| 5,743,849 A | 4/1998 | Rice et al. |
| 5,935,167 A | 8/1999 | a Wengen |
| 5,941,814 A * | 8/1999 | Lehner et al. ................... 600/25 |
| 6,168,625 B1 | 1/2001 | Prescott |
| 6,203,571 B1 | 3/2001 | Magnan et al. |
| 6,235,056 B1 | 5/2001 | Kennedy |
| 6,315,710 B1 * | 11/2001 | Bushek et al. .................. 600/25 |
| 6,379,363 B1 | 4/2002 | Herrington et al. |
| 6,387,128 B1 | 5/2002 | Kurz et al. |

(Continued)

FOREIGN PATENT DOCUMENTS

EP         224080 B1     7/1992

(Continued)

OTHER PUBLICATIONS

Design Considerations for Length Variable Prostheses Finite Element Model Simulations, Matthias Bornitz et al, Middle Ear Mechanics in Research and Otology (pp. 153-160) 2004.

*Primary Examiner* — Paul Prebilic
*Assistant Examiner* — Andrew Iwamaye
(74) *Attorney, Agent, or Firm* — Gordon & Jacobson, PC

(57) ABSTRACT

An ossicular replacement prosthesis includes first and second engagement structures for engaging middle ear structures, a spring that biases the first and second engagement structures longitudinally apart when under compression, and a rod that axially stabilizes longitudinal movement of the first and second engagement structures and conducts sound waves between the first and second engagement structures. Relative axial pressure on the first and second engagement structures causes compression or expansion of the spring which results in movement of the rod to adjust the length of the prosthesis to accommodate changes in anatomical distance as occurs under changes in pressure or abnormal middle ear conditions.

1 Claim, 5 Drawing Sheets

U.S. PATENT DOCUMENTS

| | | | |
|---|---|---|---|
| 6,398,717 B1 * | 6/2002 | Leysieffer et al. | 600/25 |
| 6,432,139 B1 | 8/2002 | Elies et al. | |
| 6,456,886 B1 | 9/2002 | Howard et al. | |
| 6,860,895 B1 | 3/2005 | Akerfeldt et al. | |
| 6,942,696 B1 | 9/2005 | White et al. | |
| 7,273,447 B2 * | 9/2007 | Schneider et al. | 600/25 |
| 7,553,328 B2 * | 6/2009 | Steinhardt et al. | 623/10 |
| 7,955,386 B2 * | 6/2011 | Reitan et al. | 623/10 |
| 2001/0016678 A1 * | 8/2001 | Kennedy | 600/25 |
| 2001/0031908 A1 * | 10/2001 | Buschek et al. | 600/25 |
| 2003/0097178 A1 | 5/2003 | Roberson | |
| 2004/0044365 A1 | 3/2004 | Bachman | |
| 2004/0181256 A1 | 9/2004 | Glaser | |
| 2005/0228213 A1 * | 10/2005 | Schneider et al. | 600/25 |
| 2005/0228214 A1 * | 10/2005 | Schneider et al. | 600/25 |
| 2005/0228215 A1 * | 10/2005 | Schneider et al. | 600/25 |
| 2006/0106418 A1 | 5/2006 | Seibold et al. | |
| 2007/0021833 A1 * | 1/2007 | aWengen et al. | 623/10 |
| 2007/0055092 A1 * | 3/2007 | Easter et al. | 600/25 |
| 2007/0055372 A1 * | 3/2007 | Prescott et al. | 623/10 |
| 2007/0083263 A1 * | 4/2007 | Steinhardt et al. | 623/10 |
| 2007/0255405 A1 * | 11/2007 | Reitan et al. | 623/10 |
| 2008/0051623 A1 * | 2/2008 | Schneider et al. | 600/25 |
| 2008/0058927 A1 * | 3/2008 | Brosnahan | 623/10 |
| 2008/0195201 A1 * | 8/2008 | Steinhardt et al. | 623/10 |
| 2009/0043149 A1 * | 2/2009 | Abel | 600/25 |
| 2009/0088844 A1 * | 4/2009 | Keegan et al. | 623/10 |
| 2009/0149697 A1 * | 6/2009 | Steinhardt et al. | 600/25 |
| 2009/0198334 A1 * | 8/2009 | Kraus | 623/10 |
| 2010/0317914 A1 * | 12/2010 | Puria et al. | 600/25 |
| 2011/0046731 A1 * | 2/2011 | Wiens et al. | 623/10 |
| 2011/0054607 A1 * | 3/2011 | Reitan et al. | 623/10 |

FOREIGN PATENT DOCUMENTS

| | | |
|---|---|---|
| FR | 2691354 A1 * | 11/1993 |
| GB | 2275422 | 2/1994 |
| WO | WO 9218066 A1 * | 10/1992 |

* cited by examiner

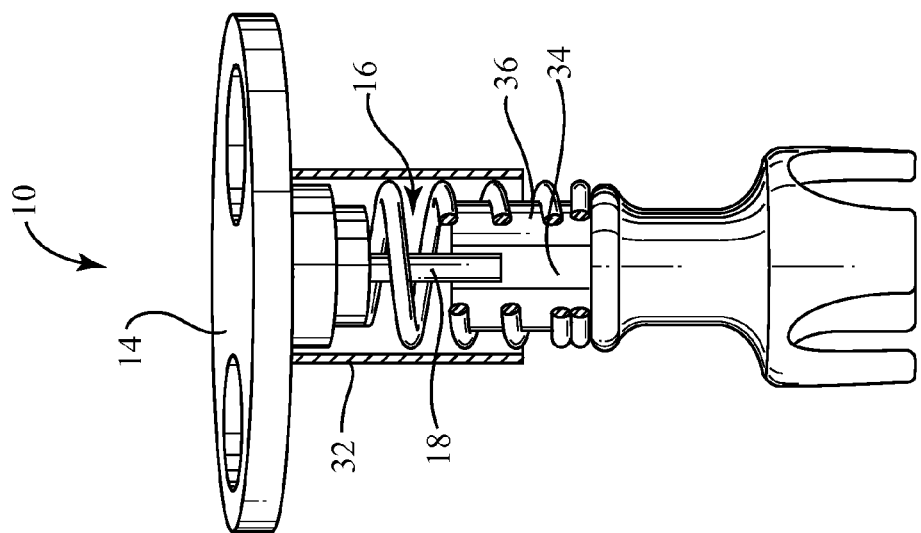
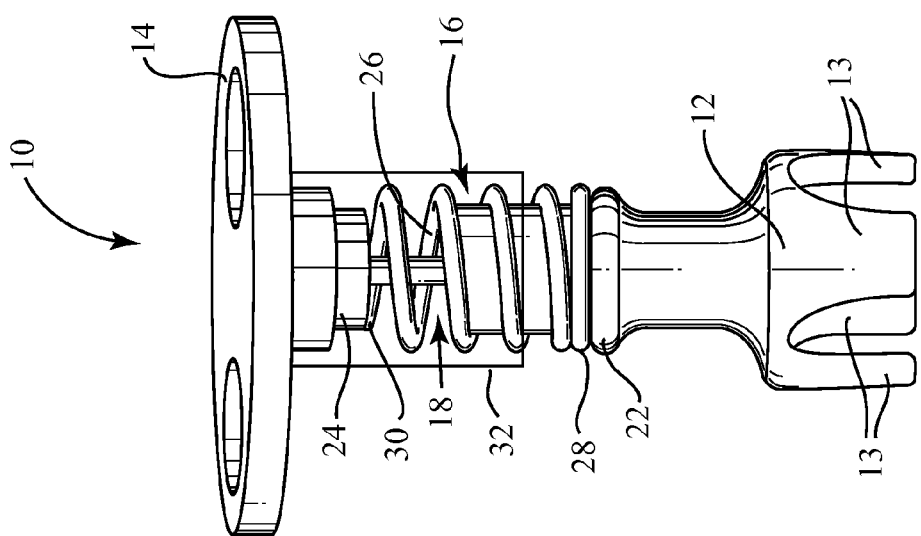

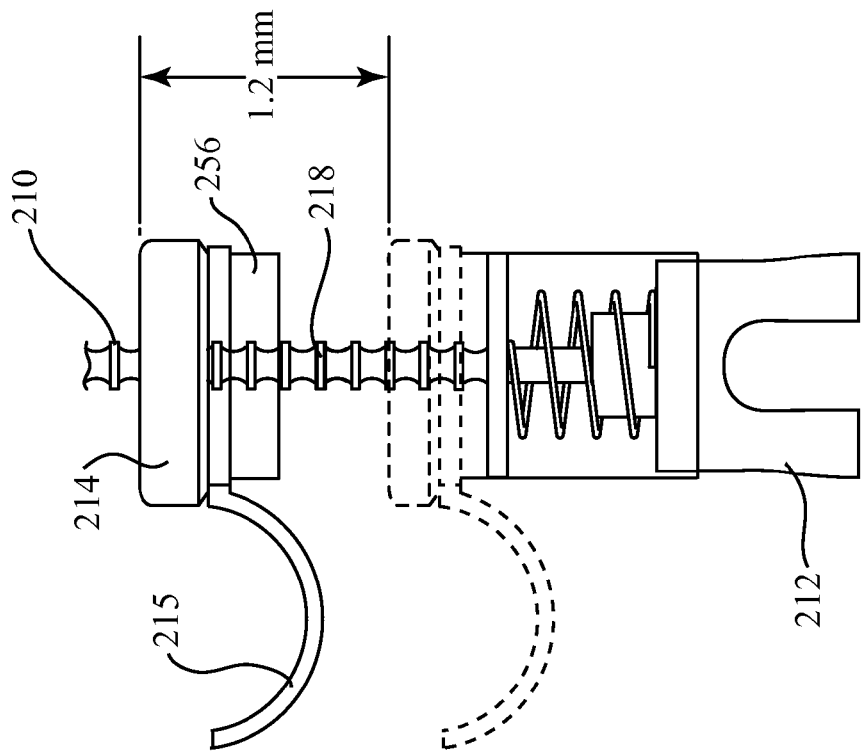
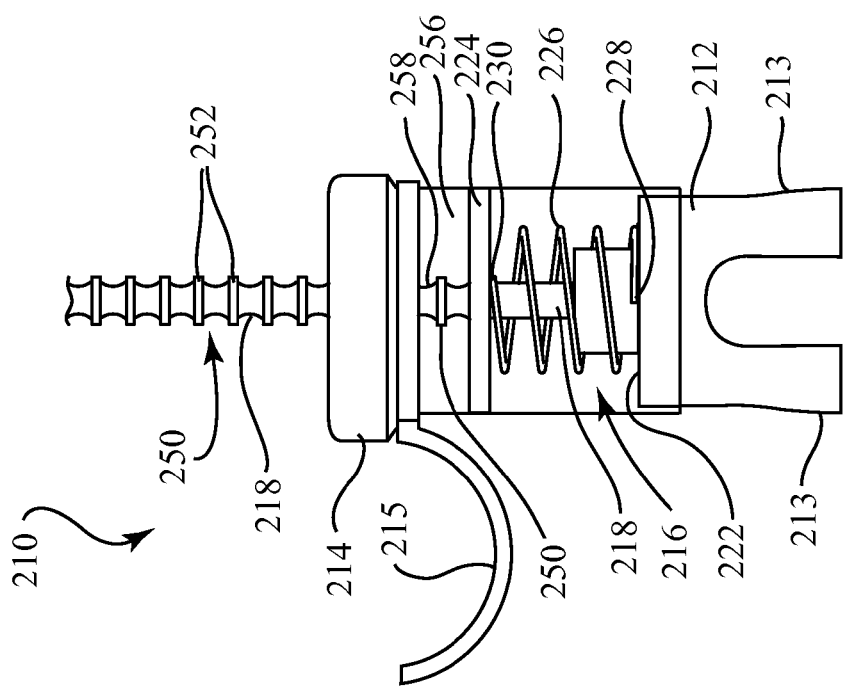

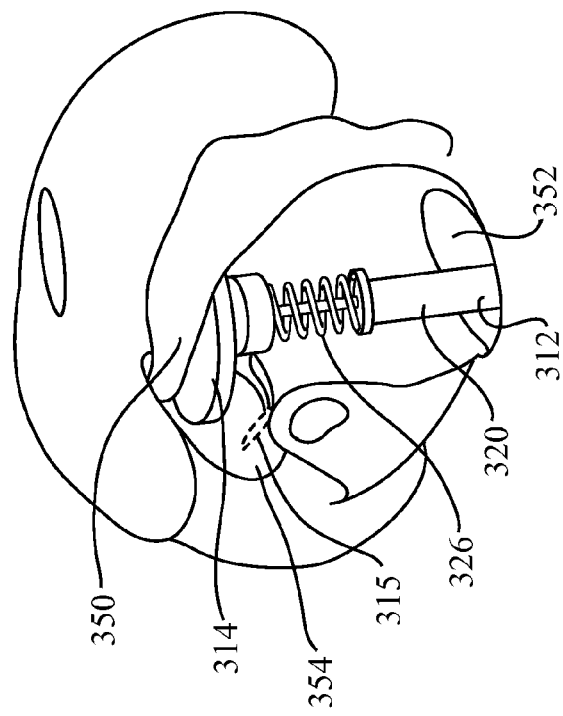
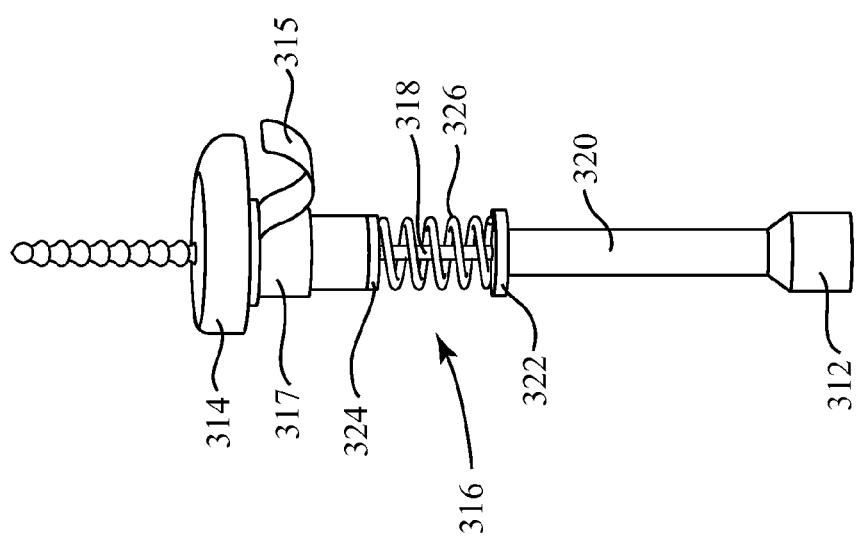
Fig. 8
Fig. 7

DYNAMIC OSSICULAR PROSTHESIS

CROSS-REFERENCE TO RELATED APPLICATION

This application claims the benefit of U.S. Provisional Application No. 61/078,929, filed Jul. 8, 2008, which is hereby incorporated by reference herein in its entirety.

BACKGROUND OF THE INVENTION

1. Field of the Invention

This invention relates broadly to prostheses. More particularly, this invention relates to prostheses for the total or partial replacement of ossicles in the middle ear.

2. State of the Art

Hearing is facilitated by the tympanic membrane transforming sound in the form of acoustic sound waves within the outer ear into mechanical vibrations through the chain of ossicular bones (malleus, incus, stapes) in the middle ear. These vibrations are transmitted through the ossicular bones to the footplate of the stapes where micro or macro motion of this structure results in compression waves within the fluid of the inner ear. These compression waves lead to vibrations of the cilia (hair cells) located within the cochlear where they are translated into nerve impulses. The nerve impulses are sent to the brain via the cochlear nerve and are interpreted in the brain as sound.

Hearing efficiency can be lost to erosion of the ossicular bones. Various combinations or portions of the bones can be replaced. For example, all of the ossicles between the tympanic membrane and the stapes footplates can be replaced using a total ossicular replacement prosthesis, or TORP. Alternatively, the malleus and incus can be replaced leaving all or a portion of the stapes intact. The prosthesis for such a procedure is a partial ossicular replacement prosthesis, or PORP.

Depending on the ossicular replacement, various different configurations of prostheses can be used. For example, a TORP generally extends from the tympanic membrane to the footplate of the stapes, and distributes force from its head end at the tympanic membrane to its distal end (shoe) positioned on the footplate. A PORP generally extends from the tympanic membrane to the capitulum and/or junction of the crura of the stapes. The proximal end of the PORP includes a head that distributes force across the tympanic membrane and the distal end includes a bell or cup that seats over the capitulum and crura of the stapes.

For each type of ossicular prosthesis, several lengths must be provided given the natural differences in anatomical distances between middle ear structures in different patients. This requires that a device company manufacture, and that a surgeon (or medical facility) inventory, various sized prosthesis to accommodate the variations in dimensions across the anatomy of patients.

Moreover, due to ambient or dynamic changes in pressure within the middle ear after implantation, e.g., by sneezing or high sound pressure levels (SPL) caused by an intense noise, the distance between prosthesis coupling points can change. This may situation may result in dislodgement of the prosthesis or otherwise lead to poor sound conduction along the ossicular chain. Further, post-operative scarring down can lead to the implanted device being too long, possibly resulting in a negative effective on sound conduction. Spring elements have been considered to accommodate the change in distance that occurs during pressure changes. Bornitz, Design Considerations for Length Variable Prostheses Finite Element Model Simulations, *Middle Ear Mechanics in Research and Otology:* 153-160 (2004), states that good sound conduction is provided by prostheses with stiff springs, but that such springs provide only very small amounts of compression ($\leq 0.02$ mm under a static load of 5 mN), which is insufficient to accommodate the change in distance under pressure. Bornitz also determined that a soft spring can provide a suitable change in compression (up to 0.53 mm under a static load of 5 mN force), but has unacceptably poor sound transfer characteristics.

SUMMARY OF THE INVENTION

An adjustable ossicular replacement prosthesis includes first and second engagement structures for engaging middle ear structures, a spring assembly that biases the first and second engagement structures longitudinally apart when under compression, and a piston assembly that facilitates longitudinal movement of the first and second engagement structures and facilitates the conduction of sound waves through the prosthesis.

In various embodiments, the adjustable prosthesis contacts or engages a membrane (with or without ossicle) at one end and contacts or engages the stapes or footplate at the other end, and even after permanent adjustment to a correct length for the patient, remains compressible and expandable along that length when implanted (in vivo).

The spring assembly preferably includes a coil spring extending between a spring stabilizer at the first engagement structure and a spring platform fixed relative to a rod of the piston assembly. The piston assembly includes an axially movable rod that is slidably disposed within a hollow body of the spring stabilizer at the second engagement structure.

Relative axial pressure on the first and second engagement structures causes compression of the spring which results in movement of the rod into the hollow body (or shoe) to compress the length of the prosthesis to accommodate changes in anatomical distance as occurs under changes in pressure. The system accommodates at least 0.25 mm and preferably 5 mm of length change.

According to one exemplar embodiment, the prosthesis is a PORP and the first engagement structure is a flanged cup for placement on the stapes, and the second engagement structure is a flat head for placement against the tympanic membrane and an adjoining open hook for engagement of the long process of the malleus (when present). The spring platform in both such embodiments is provided at the underside of the flat head. Further according to this embodiment, the spring platform is fixed on the rod and the spring is located distal of the spring platform (i.e., toward the cup). The maximum length of the rod (and prosthesis) can be permanently adjusted for a particular patient by moving the head to adjust the effective length of the rod between the first and second engagement structures, and then removing the additional protruding length (above the head), e.g., with a cutter. The lower portion of the rod will only travel through the receptacle as anatomically permitted. Thus, the replacement prosthesis is permanently adjustable in length to accommodate different patient anatomies, and the spring assembly remains capable of the full range of movement, both expansion and compression, even after the prosthesis is so adjusted in length.

According to another exemplar embodiment, the prosthesis is a TORP and the first engagement structure is a shoe for placement on the stapes footplate, and the second engagement structure is a head for placement against the tympanic membrane. The prosthesis is similarly adjustable, both permanently by the physician and post-implantation under stresses encountered in vivo.

The prostheses of the invention have very good sound transmission characteristics. The displacement of the system at 100 dB SPL across a significant audible spectrum substantially approximates an intact ossicular chain.

Additional objects and advantages of the invention will become apparent to those skilled in the art upon reference to the detailed description taken in conjunction with the provided figures.

BRIEF DESCRIPTION OF THE DRAWINGS

FIG. 1 is a side elevation of a first embodiment of an ossicular prosthesis for a partial ossicular replacement procedure according to the invention, shown in an uncompressed configuration.

FIG. 2 is similar to FIG. 1, with portions shown in broken and partial sections to illustrate an inner mechanism of the ossicular prosthesis.

FIG. 3 is a side elevation of a second embodiment of an ossicular prosthesis for a partial ossicular replacement procedure according to the invention, shown in an uncompressed configuration and prior to length adjustment.

FIGS. 4 and 5 are side elevations similar to FIG. 3 showing the prosthesis being adjusted in length.

FIG. 7 is a perspective side view of a third embodiment of an ossicular prosthesis for a total ossicular replacement procedure according to the invention, shown in an uncompressed configuration.

FIG. 8 illustrates the prosthesis of FIG. 7 shown implanted in the middle ear.

DETAILED DESCRIPTION OF THE PREFERRED EMBODIMENTS

Figure 6:
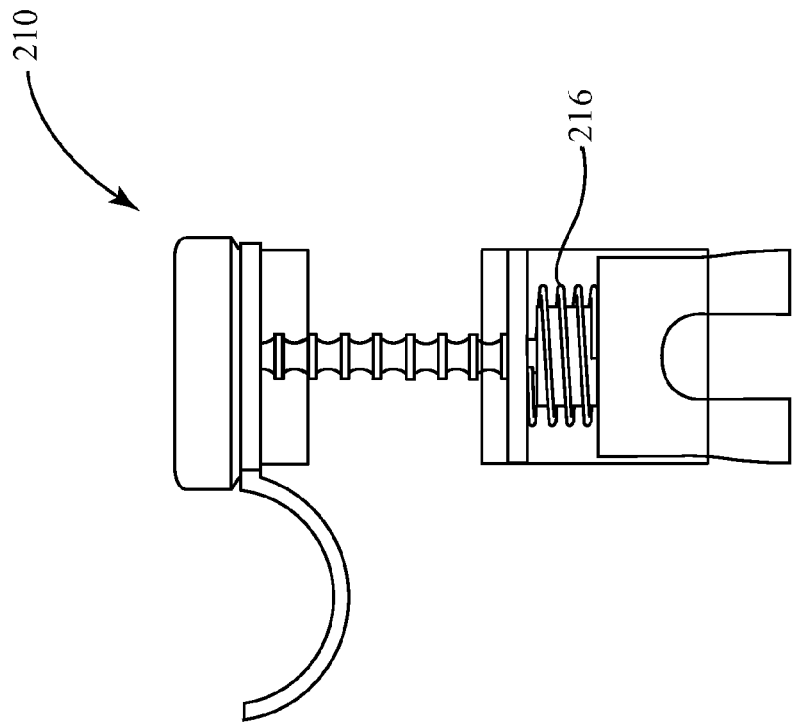
FIG. 6 is a side elevation of the prosthesis of FIG. 3 after length adjustment and in a compressed configuration.

Turning now to FIG. 1, a first embodiment of an ossicular replacement prosthesis 10 is shown and is adapted for a partial ossicular replacement between the tympanic membrane and the head of the stapes, thereby replacing the non-functional malleus and the incus. The prosthesis 10 includes a bell head or cup 12 at a first end that seats over and engages the capitulum and which is provided with a plurality of flanges 13 that at least partially surround the crura of the stapes, and a head 14 at a second end for placement at or adjacent the tympanic membrane. The head may directly contact the tympanic membrane (or a graft replacement thereof), or be adjacent by way of tissue interposed between the head and the tympanic membrane. A spring assembly 16 biases the cup 12 and head 14 longitudinally apart, and a rod 18 facilitates longitudinal movement between the cup 12 and head 14 and provides a path of sound conduction therebetween.

The spring assembly 16 includes a preferably lower spring platform 22 fixed relative to the cup 12 at the first end, an upper spring platform 24 fixed relative to the head 12 and rod 18, and a coil spring 26 having first and second ends 28, 30 welded, respectively, to the lower and upper spring platforms 22, 24. The coil spring 26 is preferably made from approximately 0.1 mm titanium wire and preferably includes three to fifteen helical windings. In a preferred embodiment, the spring 26 has a spring constant of approximately 3 gm/mm.

Optionally, a protective skirt 32 can be provided about the spring assembly 16 to keep debris and tissue from contacting the components of the spring assembly and potentially interfering with the movement thereof, and to prevent the spring 26 from potentially contacting the anatomy and causing any negative impact thereto. The skirt 32 is preferably made from a thin material such as a 0.05 mm sleeve made from, e.g., polytetrafluoroethylene (PTFE), polyethylene or silicone, so as to not impede movement of the spring assembly 16 during compression and expansion.

The rod 18 extends coaxially through the coil spring 26 and reciprocates within the axial bore 34 of a cylindrical stabilizer 36 mounted on the lower spring platform 22. The free length of the spring (when in a unbiased condition) between the top of the stabilizer 36 and the upper platform 24 is less than length of the rod 18. Therefore, the rod 18 will not unintentionally release from the axial bore 34. The rod 18 may alternatively reciprocate relative to another structure to accomplish the same result.

Relative axial pressure on the cup 12 and head 14 causes compression or expansion of the spring 26 which results in movement of the rod 18 relative to the cup 12 at the first end of the prosthesis. This motion permits the prosthesis to compress or expand about the spring to accommodate changes in anatomical distance as occurs under changes in pressure. The free length of the spring between the stabilizer 32 and the upper spring platform 24 accommodates 0.25 to 6 mm of length change for the prosthesis.

Turning now to FIG. 3, a prosthesis 210 according to a second embodiment of the invention for partial replacement of ossicles is shown. The partial ossicular replacement prosthesis 210 is adapted for placement between the stapes and tympanic membrane, replacing the function of the incus and malleus. The prosthesis 210 includes a bell cup 212 at a first end that seats over and engages the capitulum and which is provided with a plurality of flanges 213 that at least partially surround the crura of the stapes, and a head 214 at a second end for placement against the tympanic membrane. The second end is optionally provided with a malleus strap 215 for stabilizing the head relative to a non-functional malleus. The head 214 is preferably made from HA or titanium and the malleus strap 215 is preferably formed from titanium. Other suitable structures and materials can be used for engaging the tympanic membrane and malleus, if desired.

A spring assembly 216 includes a lower spring platform (e.g., upper side of cup) 222, an upper spring platform 224, and a spring 226 welded at its ends 228, 230 to the platforms 222, 224. The spring 226 biases the cup 212 and head 214 longitudinally apart when under compression, and a rod 218 axially stabilizes longitudinal movement of the cup 212 and head 214.

Figure 5:
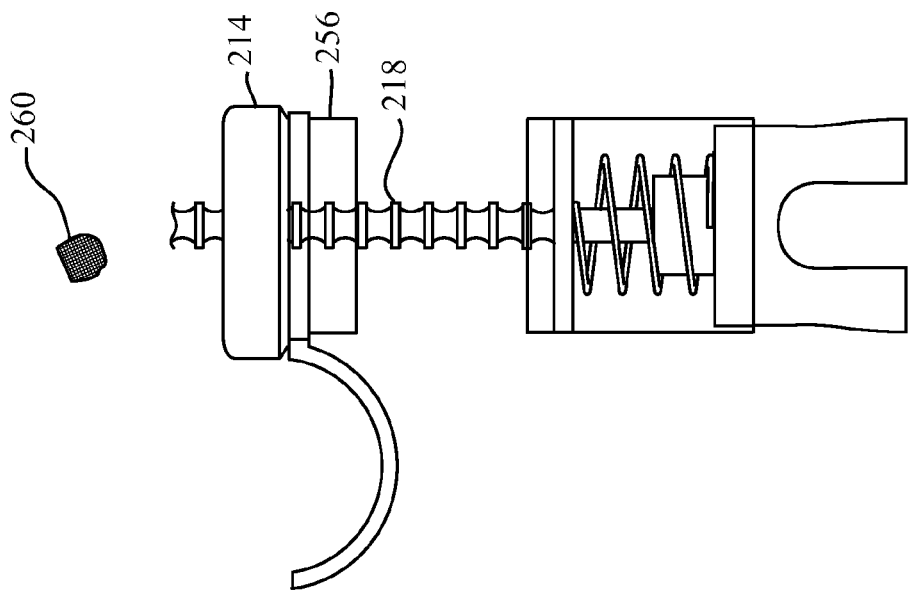

In accord with a preferred aspect of the third embodiment, but applicable to any prosthesis in accord with the invention, the upper spring platform 224 is fixed to the rod 218, and the spring 226 is located distal of the upper spring platform 224. The portion 250 of the rod 218 proximal the upper spring platform 224 includes a plurality of longitudinally spaced apart protuberances 252 (or notches). The protuberances 252 are preferably spaced apart 0.2 mm from each other, though other spacings are possible. The head 214 at the second end includes a resilient silicone sleeve 256 with a molded space that is preferably a negative image 258 of a length of the proximal portion 250 of the rod 218. The proximal portion 250 of the rod 218 resides in, and is retained within, the resilient sleeve 256. The sleeve 256 also transfers load (vibrational energy) to the rod 218. Referring to FIG. 6, the maximum length of the rod (and prosthesis) can be permanently adjusted for a particular patient by moving the proximal portion 250 of the rod 218 and the sleeve 256 relative to each other to adjust the distance between the cup 212 and head 214. By moving the sleeve 256 and rod 218 relative to each other from the positions shown in FIG. 3 to FIG. 4, the head 214 has moved further 1.2 mm relative to the cup 212. Then, referring to FIG. 5, the additional length 260 of the rod 218 protruding beyond the proximal end of the head 214 is removed, e.g., with a cutter, so that the proximal end of the rod 218 is preferably flush or slightly within with the head 214. As another alternative, a small portion of the rod 218 can be left protruding from the head to enhance stabilizing the head on tissue located between it and the tympanic membrane. Once adjusted intraoperatively by the surgeon, the proximal portion 250 of the rod 218 will not travel through the sleeve 256 under the physiological forces encountered in the ear. Thus, the prosthesis is permanently adjustable in length to accommodate different patient anatomies. The prosthesis in FIG. 5 is adapted for a patient needing a prosthesis 1.2 mm longer than the prosthesis shown in FIG. 3. Referring to FIG. 6, it is seen that even after permanent maximum length adjustment of the prosthesis 210, the spring assembly 216 remains effective to accommodate significant compression under axial pressure. An axial adjustment of 0.5 mm under compression is shown. Further, the prosthesis can accommodate post-implantation expansion. The prosthesis can be implanted with a slight amount of compressive pre-load. For example, the prosthesis may be compressed, e.g., 0.10 mm to 0.25 mm during implantation. Then, post-operatively, the load assists to maintain stability of the implant at the implantation site.

Turning now to FIG. 7, a third embodiment of an ossicular replacement prosthesis 110 is shown and is adapted for a total ossicular replacement between the stapes footplate and the tympanic membrane. The prosthesis 310 includes a shoe 312 at a first end for engagement against the stapes footplate, and a head 314 at a second end for engagement against the tympanic membrane. The shoe 312 is preferably made from titanium. The head 314 is preferably made from titanium or hydroxylapatite (HA) and includes a resilient sleeve 317 and a malleus strap 315, both as described with respect to head 214. The head 314 is attached to a rod 318. A spring assembly 316, generally as described above, biases the shoe 312 and head 314 longitudinally apart. The rod 318 axially stabilizes longitudinal movement of the shoe 112 and head 114, as described with respect to the prosthesis 210. The head 314 is manually adjustable along the proximal end of a rod 318, which is then trimmable to length, as also described above with respect to prosthesis 210. A shaft 320 extends between the shoe 312 and the spring assembly 316 to provide necessary length to the prosthesis.

Referring to FIG. 8, the prosthesis 310 is shown implanted in the middle ear replacing function of the malleus, incus, and the superstructure of the stapes. The shoe 312 at the end of the shaft 320 is seated on the stapes footplate 352. The head 314 is placed against the tympanic membrane 350, with the malleus strap 315 stabilized relative to the malleus 354. The spring 326 is not under modest compression as shown, but under pressure (e.g., from sneezing or high SPL) the spring 326 will compress, permitting the head 314 and shoe 312 to move toward each other as the anatomical distance between their respective coupling points changes. The prosthesis, after adjustment of the head on the rod, can accommodate a change in length of, e.g., up to 6 mm. In addition, the prosthesis can be compressed to aid in implantation.

Further, with respect to each of the prostheses, once positioned within the middle ear, the spring provides the prosthesis with a pre-load against the respective middle ear structure that provides increased stability. This is particularly important during initial months post-implantation when prostheses can be unstable and most susceptible to dislodgement.

Figure 9:
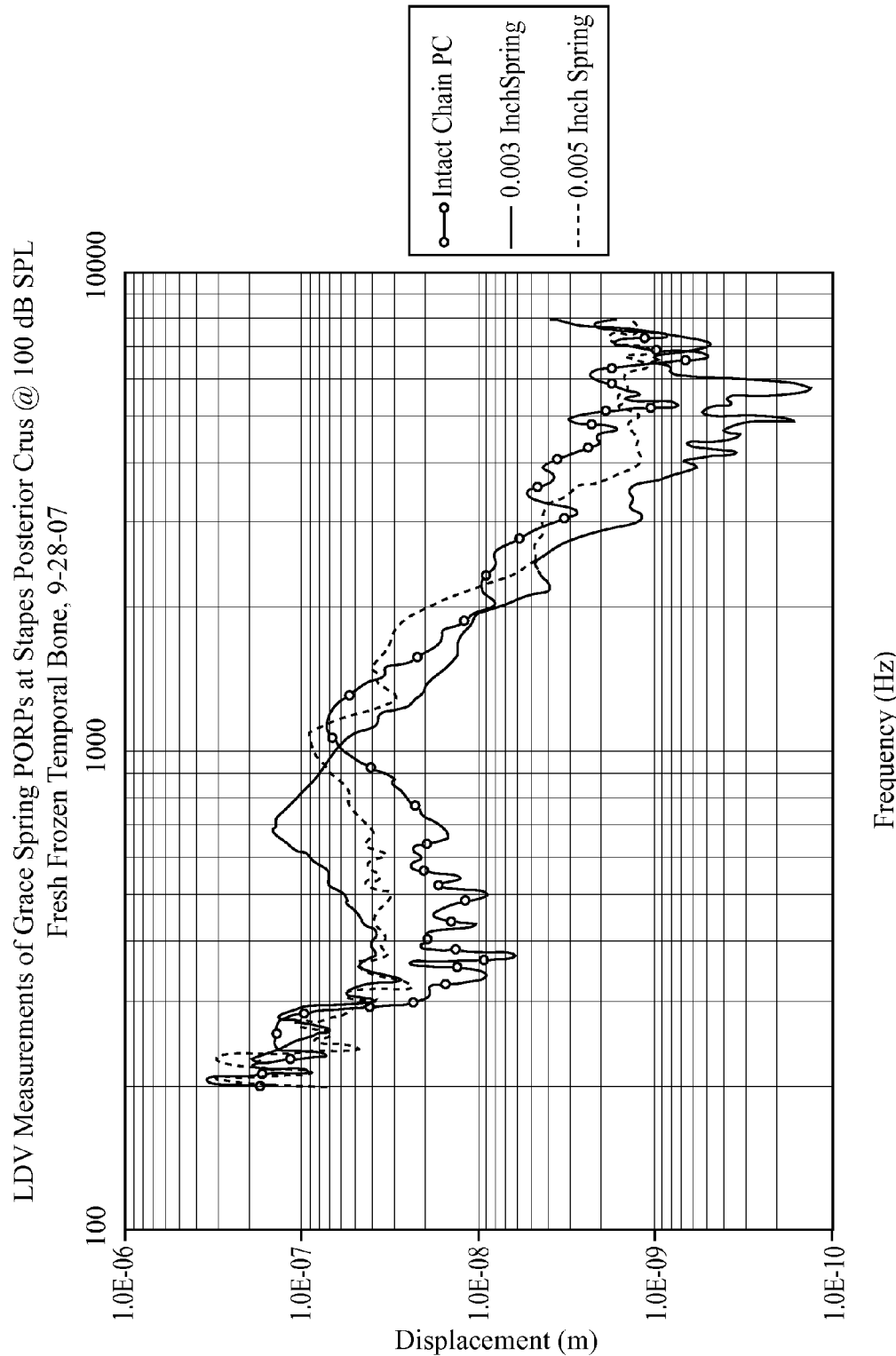
FIG. 9 graphs displacement versus frequency in response to a 100 dB SPL sound stimulus for laser doppler vibrometry measurements at the stapes for the implanted third embodiment of the invention as compared to measurements of the intact ossicular chain, in a fresh frozen human temporal bone.

Referring to FIG. 9, to test the responsiveness of the prostheses, laser doppler vibrometry tests were performed comparing a total ossicular replacement prosthesis according to the invention with an intact ossicular chain (fresh frozen temporal bone). The tests compared the displacement at various frequencies for a 100 dB SPL stimulus applied to the ear canal. Measurements were made at the posterior crus of the stapes. It is initially evident that the measurements of the prosthesis tracked the intact ossicular chain very well. The relative movement at the various frequencies indicate that the performance of the prosthesis using a spring manufactured from 0.003 inch (0.076 mm) diameter wire relative to a spring wound from 0.005 inch (0.127 mm) diameter wire, while slightly different, both track the intact ossicular chain very well.

There have been described and illustrated herein several embodiments of an ossicular prosthesis. While particular embodiments of the invention have been described, it is not intended that the invention be limited thereto, as it is intended that the invention be as broad in scope as the art will allow and that the specification be read likewise. Thus, while particular ossicular engagement structures have been shown, it will be appreciated that other engagement structures for engaging other anatomical structures can be used as well. For example, while the tympanic membrane has been shown engaged by a TORP, a prosthesis that includes a strap without a tympanic membrane contacting element can be used, with the primary engagement made between the malleus (at the strap) and the stapes footplate. Similarly, for a PORP, the prosthesis may be configured to extend between the malleus, with, e.g., an inline curved brace at one end, and the stapes capitulum, with a cup at the other end. Also, while several preferred materials have been disclosed, it is appreciated that other suitable materials can be used as well. In addition, while particular means for attaching the spring to the respective distal and proximal ends of the prosthesis have been disclosed (i.e., welds and platforms), it is appreciated that other means may be used as well. For example, welds, bonding agents or mechanical engagements may be used with or without platforms. The described prostheses have maximum lengths ranging between 1.75 and 8 mm. Further, while a preferred spring compression is disclosed, where a smaller or larger spring compression is permitted, the prosthesis may be constructed in slightly different minimum and maximum lengths from those disclosed above. It will therefore be appreciated by those skilled in the art that yet other modifications could be made to the provided invention without deviating from its spirit and scope as claimed.

What is claimed is:

1. An ossicular prosthesis, comprising:
 a) a first prosthesis portion having a first end for engaging a first middle ear structure;
 b) a second prosthesis portion having a second end for engaging a second middle ear structure;
 c) a spring that biases the first and second prosthesis portions longitudinally apart and which is expandable or compressible to self adjust a length of said prosthesis when said first and second prosthesis portions are subject to axial forces, said spring having first and second ends and defining an internal space;

d) a rod extending within the internal space of the spring and longitudinally displaceable within the internal space upon longitudinal movement of said first and second prosthesis portions relative to each other, said rod including a plurality of protuberances, said second prosthesis portion including a resilient member defining a negative space adapted to retain a portion of said rod provided with said protuberances, wherein said rod and said resilient member can be forced relative to each other to alter the maximum distance between said first and second ends of said first and second prosthesis portions but wherein physiological forces encountered in the middle ear are insufficient to move said rod relative to said resilient member.

* * * * *